(12) United States Patent (10) Patent No.: US 8,977,334 B2
Greenspan et al. (45) Date of Patent: Mar. 10, 2015

(54) CATHETER SYSTEMS FOR MEASURING ELECTRICAL PROPERTIES OF TISSUE AND METHODS OF USE

(71) Applicants: Albert Einstein Healthcare Network, Philadelphia, PA (US); The Trustees of the University of Pennsylvania, Philadelphia, PA (US)

(72) Inventors: Allan M. Greenspan, Philadelphia, PA (US); Yale E. Goldman, Merion Station, PA (US)

(73) Assignees: Albert Einstein Healthcare Network, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/091,423

(22) Filed: Nov. 27, 2013

(65) Prior Publication Data

US 2014/0155722 A1 Jun. 5, 2014

Related U.S. Application Data

(63) Continuation of application No. 13/689,069, filed on Nov. 29, 2012, now Pat. No. 8,655,427.

(51) Int. Cl.
*A61B 5/042* (2006.01)
*A61B 5/053* (2006.01)
*A61B 5/0428* (2006.01)

(52) U.S. Cl.
CPC ............... *A61B 5/0538* (2013.01); *A61B 5/042* (2013.01); *A61B 2562/0209* (2013.01)
USPC ............................ 600/374; 600/393; 600/547

(58) Field of Classification Search
CPC .... A61B 5/042; A61B 5/0538; A61B 5/0402; A61B 5/0408; A61B 5/0422; A61B 5/04288; A61B 5/046; A61B 5/0464; A61B 5/053; A61B 5/6847; A61B 5/6852; A61B 5/6896; A61B 5/6885; A61B 5/7203; A61B 5/7214; A61B 5/7285; A61B 2017/00026; A61B 2017/00703; A61B 2562/0209; A61B 2562/046; A61B 2562/182
USPC .......... 600/372–374, 393, 509, 515, 518, 547
See application file for complete search history.

(56) References Cited

U.S. PATENT DOCUMENTS 3,452,743 A * 7/1969 Rieke ............................ 600/547
4,289,142 A 9/1981 Kearns
(Continued)

OTHER PUBLICATIONS

Normann, "Driven Shields or Guard Rings" in Principles of Bioinstrumentation, pp. 193-194, Wiley & Sons, (1988).*
(Continued)

*Primary Examiner* — Linda Dvorak
*Assistant Examiner* — Erin M Cardinal
(74) *Attorney, Agent, or Firm* — Caesar, Rivise, Bernstein, Cohen & Pokotilow, Ltd.

(57) ABSTRACT

Catheter systems for measuring at least one electrical property, e.g., impedance, of cardiac tissue of a living being are disclosed. The system includes a catheter having a tip with a sensing electrode, a guard electrode and an electrical shield. The sensing electrode is arranged to engage the cardiac tissue and is coupled to circuitry for measuring the at least one electrical property of the cardiac tissue, shielding the sensing electrode from bulk blood adjacent the cardiac tissue. The measurement can gated to the cardiac cycle. Additional embodiments include multi-electrode sensor catheter tips for high density mapping. Moreover, such tips may be dynamically configurable, i.e., their electrodes can be variably assigned as sensor electrodes or guard electrodes by associated circuitry. Such multi-electrode configuration and reconfiguration can be gated to the cardiac cycle.

5 Claims, 2 Drawing Sheets

(56) References Cited

U.S. PATENT DOCUMENTS

| | | | |
|---|---|---|---|
| 5,109,861 A * | 5/1992 | Walinsky et al. | 600/463 |
| 5,361,762 A * | 11/1994 | Gunter | 600/372 |
| 5,588,429 A | 12/1996 | Isaacson et al. | |
| 5,836,990 A * | 11/1998 | Li | 607/28 |
| 6,073,039 A | 6/2000 | Berson | |
| 6,522,904 B1 | 2/2003 | Mika et al. | |
| 8,301,219 B2 | 10/2012 | Chen et al. | |
| 2004/0158167 A1 | 8/2004 | Smith et al. | |
| 2006/0058694 A1 | 3/2006 | Clark et al. | |
| 2010/0079156 A1 | 4/2010 | Lee | |

OTHER PUBLICATIONS

Narayanan Namboodiri, Electroanatomic Contact Mapping: How to Use Optimally to Recognise the Arrhythmia Mechanism? Indian Pacing and Electrophysiology Journal, Jul. 10, 2012, pp. 1 to 13.

* cited by examiner

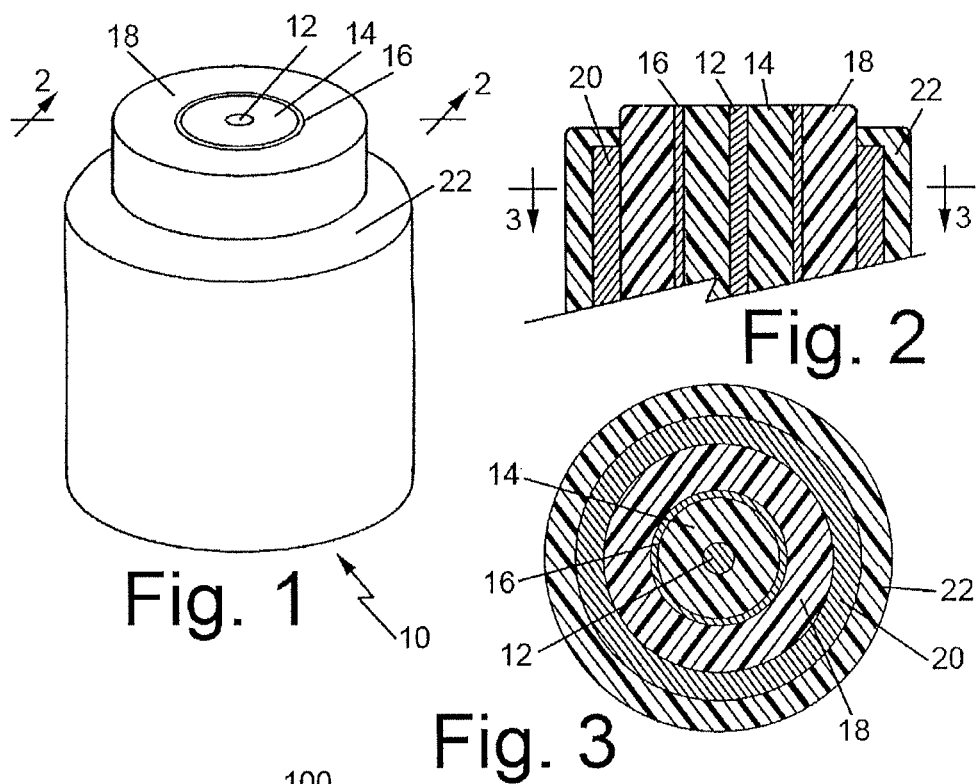
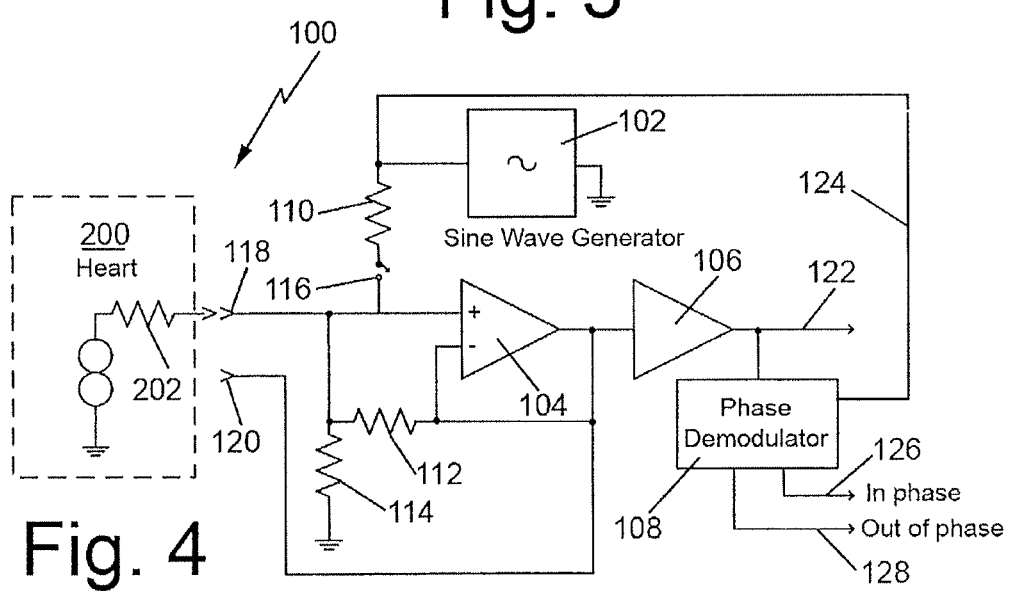

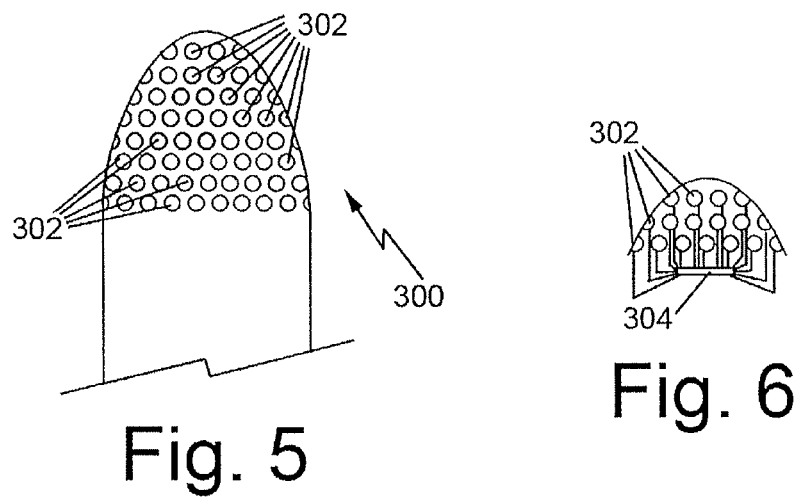
Fig. 5
Fig. 6
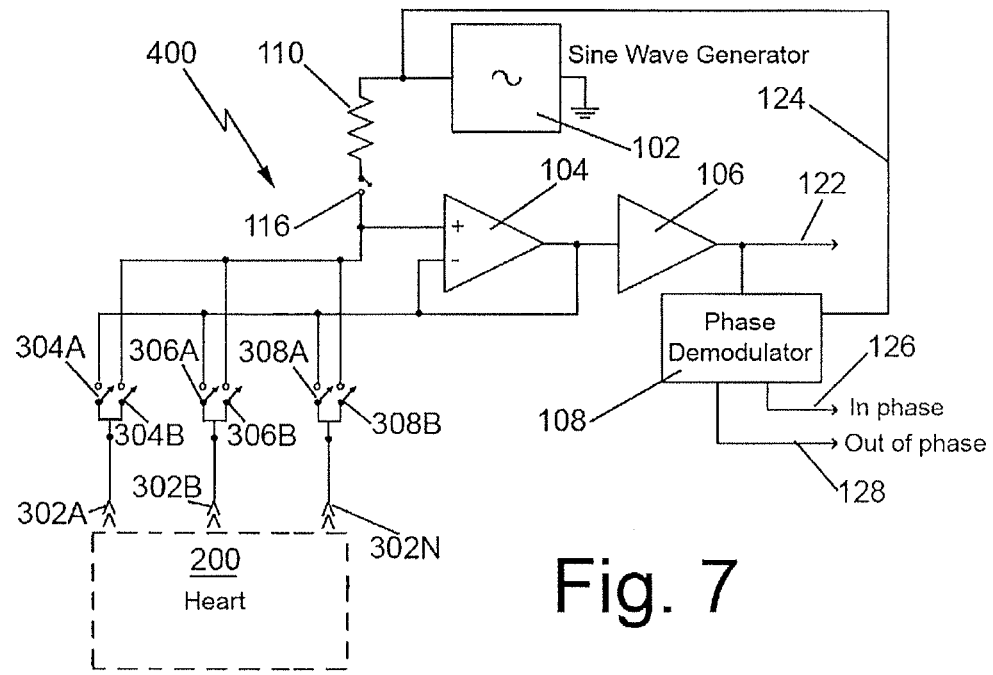
Fig. 7

CATHETER SYSTEMS FOR MEASURING ELECTRICAL PROPERTIES OF TISSUE AND METHODS OF USE

CROSS-REFERENCE TO RELATED APPLICATIONS

This utility application is a continuation under 35 U.S.C. §120 of non-provisional patent application Ser. No. 13/689,069 filed on Nov. 29, 2012, which issued as U.S. Pat. No. 8,655,427 B1 on Feb. 18, 2014 and is entitled Catheter Systems for Measuring Electrical Properties of Tissue and Methods of Use, the entire disclosures of which are incorporated by reference herein.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to catheter systems and methods of use for measuring electrical properties and signals in the heart of a living being.

BACKGROUND OF THE INVENTION

This invention entails a new apparatus for measuring electrical properties of the heart, including but not limited to impedance. The usefulness of measuring impedance is discussed at length in co-pending U.S. non-provisional patent application Ser. No. 13/604,168, entitled Cardio Mapping System and Method of Cardio Mapping, filed on Sep. 5, 2012, which is assigned to, Albert Einstein Healthcare Network, one of the two assignees of the subject invention.

In particular, that application, whose disclosure is specifically incorporated herein, entails apparatus and methods for arrhythmia discrimination system and methods for determining the mechanism of cardiac arrhythmia in a patient. The cardiac arrhythmia discrimination system of that application comprises a catheter and an associated processing unit. The catheter and the processing unit are arranged to measure the electrical impedance (hereinafter "impedance") of cardiac tissue of the patient at various selected points on the endocardial/epicardial surface of the patient's heart during a spontaneously occurring or induced arrhythmia, e.g., supraventricular tachycardia, and providing the geometric position of each of the points on the patient's heart. Each of the impedance measurements and point positions are recorded by the system. The system is arranged to determine if a point on the patient's heart exhibits low impedance ($Z_{low}$), wherein $Z_{low} \leq Z_{min} + 0.1 (Z_{max} - Z_{min})$, where $Z_{min}$ is the minimum impedance measured and $Z_{max}$ is the maximum impedance measured. The system is also arranged to discard from its impedance measurements any points associated with tissue voltage of less than 0.5 mV indicating poor contact of the catheter to the cardiac tissue, as well as any points that are too internal to the anatomic shell (e.g., >1 mm internal to a 15 degree spherical arc of curvature with a radius of 1.5-2 cm inscribed by a local group of measured points on the heart chamber shell) or points with far-field low amplitude electrograms, and evaluates the remaining points of measured impedance to determine if there is an area of a predetermined size, e.g., approximately 3.4±2 cm² or 2.4±1.8% of the atrial surface area, having plural $Z_{low}$ points therein. The system is also used for identifying coherent, rapidly conducting pathways that may be participating in reentrant circuits and to identify damaged cardiac tissues, i.e., scar tissue, that is often the substrate for micro-reentrant circuits. In accordance with one preferred aspect of that invention, the system includes a video display coupled to the processing unit and which is arranged to produce an iso-impedance map of the cardiac tissue. The iso-impedance map is colored to represent differing impedances measured by the catheter to enable a user of the system to visually analyze the color pattern of the iso-impedance map to differentiate a focal arrhythmia caused by a group of cells focally firing, from a reentrant arrhythmia caused by a macro-reentrant circuit. The iso-impedance map can be used to facilitate appropriate therapy, e.g., ablation.

Currently catheter-based measurement of local activation time, tissue voltage, and, as recently proposed in the foregoing copending patent application, tissue impedance of the heart, are used to analyze mechanisms of cardiac arrhythmias. Current catheter technology (with large surface area electrodes) results in a considerable shunt conductance that reduces amplitude and fidelity of the recorded signals and diminishes the ability to analyze arrhythmia mechanisms.

Present mapping practice involves contact of an electrical lead to the myocardium. Various electrical resistances and conductances exist in this electrical circuit. A particularly troublesome component is the shunt conductance which exists between the electrode and the surrounding blood and which attenuates all of the recorded signals substantially. Thus, there exists a need for an improved catheter that is less sensitive to the shunt conductance and which will improve the fidelity and ease of mapping such signals. The subject invention addresses that need and other needs.

All references cited herein are fully incorporated.

SUMMARY OF THE INVENTION

One aspect of this invention entails a catheter for introduction into the body of a living being for measuring at least one electrical property, e.g., impedance, of cardiac tissue of the being. The catheter has a distal end comprising a sensing electrode, a guard electrode and an electrical shield. The sensing electrode is arranged to engage the cardiac tissue and coupled to circuitry for measuring at least one electrical property of the cardiac tissue. The guard electrode surrounds the sensing electrode and is arranged for engaging the cardiac tissue and shielding the sensing electrode from bulk blood adjacent the cardiac tissue. The electrical shield surrounds the guard electrode.

In accordance with another aspect of the invention, the catheter is part of a system which comprises a follower amplifier and wherein a voltage appears at the sensing electrode. The follower amplifier is arranged to apply a signal to the guard electrode to maintain the potential of the guard electrode at approximately the same voltage as the voltage appearing at the sensing electrode.

In accordance with another aspect of this invention, the system comprises electronic control circuitry and wherein the sensing electrode comprises at least one of a plurality of electrodes, and the guard electrode comprises a subset of the plurality of electrodes. The control circuitry is coupled to the plurality of electrodes for selecting which of the plurality of electrodes forms the at least one sensing electrode and which of the plurality of electrodes forms the subset that will form the guard electrode.

In accordance with another aspect of this invention, the control circuitry effects a time-gated electrode configuration dynamically during the cardiac cycle In accordance with another aspect of this invention, the system comprises a signal source for applying a current to the sensing electrode, whereupon a sensed voltage occurs at the sensing electrode that is indicative of the at least one electrical property, e.g., impedance, of the cardiac tissue in the vicinity of the sensing electrode.

In accordance with another aspect of this invention, the system comprises a phase demodulator arranged to receive the sensed voltage, wherein the signal source is a time-varying signal and wherein the phase demodulator indicates in-phase and quadrature components of said sensed voltage.

In accordance with another aspect of this invention, the system is arranged for detecting anisotropically conducting cardiac tissue of a living being, with the system comprising a catheter having a distal end arranged for engaging the cardiac tissue for effecting high density impedance mapping thereof. The distal end of the catheter is arranged to reduce the shunt conductance which exists between the electrode and the surrounding blood.

Another aspect of this invention entails a catheter system for identifying regions of maximal cardiac tissue stretch to help identify and localize regions of focal firing. That catheter system provides anatomic mechanical compliance measurements (henceforth termed "compliance") of cardiac tissue and comprises a pressure sensing catheter adapted to determine cardiac tissue compliance throughout various points in the atrium, e.g., the system comprises a mechanical stiffness detector to map the tissue mechanical compliance at high spatial resolution of the various point in the atrium, and wherein compliance is the reciprocal of stiffness, i.e., compliance=1/stiffness.

Still another aspect of this invention entails a catheter system which effects the time gated recording of the impedance, e.g., gating impedance measurements to electrical systole and diastole and sub-intervals within systole and diastole.

DESCRIPTION OF THE DRAWINGS

FIG. 1 is an isometric view of the distal end or tip of one exemplary catheter of a system constructed in accordance with this invention;

FIG. 2 is a sectional view taken along line 2-2 of FIG. 1;

FIG. 3 is a sectional view taken along line 3-3 of FIG. 2;

FIG. 4 is a schematic diagram of one exemplary circuit forming a portion one exemplary system making use of a catheter constructed in accordance with this invention having a sensor electrode and a guard electrode;

FIG. 5 is a side elevation view of another exemplary catheter of a system constructed in accordance with this invention;

FIG. 6 is a cross-section view of a portion of the catheter tip of FIG. 5; and

FIG. 7 is a schematic diagram of another exemplary circuit forming a portion another exemplary system for connecting the signal generator and follower amplifier of FIG. 3 to a plurality of electrodes, like those shown in FIGS. 5 and 6.

DETAILED DESCRIPTION OF THE PREFERRED EMBODIMENT

Referring now to the various figures of the drawing wherein like reference characters refer to like parts, there is shown in FIGS. 1 and 2 a mechanical arrangement of one exemplary embodiment of a catheter 10 constructed in accordance with this invention. The catheter 10 is believed to be of particular utility for use in a system or method like that disclosed in the aforementioned patent application and for other uses. For example, as is known, typical atrial flutter is caused by a macro-reentrant circuit with clearly defined anatomic barriers to conduction, which forms a critical isthmus through which the reentrant electrical currents flow. This allows a straight-forward approach to RF ablation of atrial flutter directing the application of RF energy to the anatomically delimited critical isthmus. However, there are many forms of atypical atrial flutter occurring throughout both atria where critical isthmuses involved in the macro-reentrant circuit are not delimited by well-defined anatomic barriers. Rather, they are bounded by either non-conducting scar tissue, causing anatomic conduction block, or by anisotropically conducting tissue causing functional conduction block. In many cases of atypical atrial flutter, localizing the critical isthmuses, under these circumstances is quite difficult, using standard local electrical activation time (LAT) mapping, voltage mapping and entrainment mapping. Specifically, although scar tissue may be identified by its very low tissue voltage, anisotropically conducting tissue has normal tissue voltage and escapes detection.

A possible new usage of the impedance mapping apparatus and methods of the co-pending patent application Ser. No. 13/604,168, is the detection of anisotropically conducting tissue. In this regard as discussed in that patent application, impedance mapping has been shown to identify regions of focal firing as well as structures with rapid conducting coherent muscle bundles, such as Bachman's bundle, both of which show lower tissue impedance than normally conducting tissue. Anisotropically conducting tissue, because of extremely non-coherent muscle bundle architecture, should theoretically demonstrate higher tissue impedance compared with normally conducting tissue. Thus, high density impedance mapping (e.g., >4 points/cm$^2$) in atypical atrial flutter may be able to differentiate small regions of scarring (low voltage, very low impedance) from normally conducting tissue (normal voltage, normal impedance) and from anisotropically conducting tissue (normal voltage, increased impedance). In particular, a high density impedance map could help identify the critical isthmuses that may be delimited by two regions of scar, between scar and anisotropically conducting tissue, or between two regions of anisotropically conducting tissue that form the borders of the critical isthmuses in atypical atrial flutter. This would facilitate more accurate targeting of the critical isthmuses for ablation and speed successful RF ablation of these very difficult to map macro-reentrant arrhythmias.

The catheters of this invention may prove very useful for such applications. To that end, the distal end or tip of a catheter constructed in accordance with one exemplary embodiment of this invention is shown in FIG. 1. That catheter is part of a system, to be described later for mapping electrical characteristics, e.g., impedance, of the cardiac tissue. As can best be seen in FIG. 1, the distal end of the catheter 10 includes a tip arranged for end-on contact with the myocardium (not shown) of a living being. The distal end portion of the catheter, including its tip, is constructed to block current from leaking into the surrounding bulk blood, which current leakage or shunt current can compromise the electrical parameter measurements made by the catheter. To that end, the tip 10 includes several concentric layers. In particular, the center of the catheter is in the form of a central metallic electrode 12, which serves as the sensing electrode for the system. The free end of the sensing electrode is arranged to be brought into contact with the myocardium to enable the associated system to measure the electrical parameter, e.g., impedance, desired. Surrounding the sensing electrode 12 is a first electrical insulator 14. Surrounding the first electrical insulator 14 is a guard electrode 16. The guard electrode 16 is in the form of a metallic sheath or ring. The free end of the guard electrode 16 is also arranged to be brought into contact with the myocardium and serves to shield the sensing electrode 10 from the surrounding bulk blood. Surrounding the guard electrode is a second electrical insulator 18. Surrounding the second insulator is a metallic, electromagnetic (Faraday) shield 20. Surrounding the Faraday shield is a final or outer insulating layer 22. As best seen in FIG. 2, the insulating layer 22 covers or encloses the Faraday shield to isolate it from the surrounding blood. While the free end of the sensing electrode 12 and the guard ring 16 are shown as lying in the same plane, other configurations are contemplated. For example, the tip may be more rounded, whereupon the free end of the guard ring will lie slightly below the sensing electrode in a cross-sectional view.

Turning now to FIG. 4, there is shown one exemplary circuit 100 forming a part of one exemplary mapping system for use with a catheter 10 like that described above, e.g., a catheter having a tip including a guard electrode. The circuit 100 is arranged to provide a low impedance source for the guard electrode 16, while maintaining the guard electrode at approximately the same electrical potential as the sensing electrode 12. To that end, the circuit 100 basically comprises a signal, e.g., sine wave, generator 102, a voltage follower (operational amplifier) 104, a buffer amplifier 106, a phase demodulator 108, resistors 110, 112 and 114, a switch 116, and connector 118 and 120. The sensor electrode 12 is connected via contact 118 to the juncture of resistors 112, 114, to one pole of switch 116 and to the positive input of the voltage follower 104. The guard electrode 16 is connected to the juncture of the output of the voltage follower 104, one side of resistor 112, to the negative input of the voltage follower 104 and to the input of the buffer amplifier 106. The output of the buffer amplifier 106 is connected to one input of the phase demodulator 108 and to a conductor 122. Another input to the phase demodulator is provided by line 124 from the juncture of the output of the signal generator 102 and one side of the sensor electrode source resistor 110. The conductor 122 is connected to a computer or other processor (not shown) forming a portion of the rest of the system via an analog-to-digital (A/D) converter (also not shown). The signal generator 102, supplies a sinusoidal signal of known amplitude to the sensor electrode source resistor 110 via the switch 116 when the switch is closed. The follower amplifier (e.g., a unity gain buffer amplifier) 104 provides a signal to the guard electrode 16 via contact 120. This signal maintains the potential of the guard at approximately the same voltage as the sensing electrode 12. Thus, shunt current cannot flow between the sensing electrode and guard electrode because they are at essentially the same potential, thereby greatly improving amplitude and fidelity of the measured signal.

As best seen in FIG. 4, a patient's heart 200 has resistance, which is represented by the resistor 202. That resistance appears between the contact point of the sensing electrode and ground. The sinusoidal small, harmless current flows through the switch 116 and the sensor electrode 12 into the heart 200. The resistor 202 which is shown inside the box designated "heart" represents the unknown element that the impedance measurement will be determining. The sensor electrode source resistor 110 is typically a high value, e.g., on the order of 1 megaohm. Thus, the signal appearing at the positive (+) input to operational amplifier 104 is representative of the impedance of the heart tissue between the sensor electrode and ground. This signal is buffered by the amplifier's unity gain configuration, where resistors 112 and 114 are selected to adjust the gain of the follower, as is well known in the art. The buffer (operational) amplifier 106 is provided to amplify the relatively low voltage output of the voltage follower 104 to a more useful scale for measurement. With a AC input signal from the signal generator 102, the output of amplifier 106 will track the relative resistance of the heart tissue at the location of the point at which the distal end of the sensor electrode 12 contacts that tissue. The proximity of the guard electrode 16, which is held at or near the voltage of the sensor electrode 12 prevents the bulk blood in the area from shunting the voltage from the signal generator 102. The signal appearing on line 122, being an analog signal representative of the impedance of the cardiac tissue is provided to an A/D converter (not shown) from whence it is provided to the rest of the circuitry making up the system, e.g., the circuits and associated components for providing readings of the impedance measured and for displaying an impedance map of those readings. Thus, the impedance measurements taken by the system may be displayed as an impedance map or otherwise communicated to the user of the system in the manners and by means like that described in the heretofore identified patent application, patent application Ser. No. 13/604,168.

Heart muscle has complicated circuitry, e.g., essentially it can be thought of as resistors and capacitors. Thus, the electrical signal sensed by the catheters of this invention include a component that is 90 degrees out of phase with the input sine wave. That out of phase component can provide valuable and useful information about the membrane capacitance for the cardiac tissue and about the connections between the cells. When cells become ischemic they become disconnected from each other, thus having less effective membrane area and less capacitance. Accordingly, the phase of the signal sensed by the catheter's sensing electrode can provide useful information about the condition of the cardiac tissue. As such the subject invention contemplates using the circuit 100 to measure out-of-phase impedance of the heart tissue, which is capacitive. In particular, as shown in FIG. 4, the signal generator 102 is arranged to generate a sine wave which drives both the sensor electrode and the phase demodulator 108. The phase demodulator separates the in-phase (I) and quadrature (Q) portions of the impedance. During impedance mapping using sinusoidal signals the two components 90° out of phase with each other (termed quadrature), provide information on resistance and capacitance of the sensed heart region leading to indication of the effective area being probed, connectivity between nearby myocardial sites, and inference of metabolic health of the tissue and whether or not the tissue is ischemic. The in-phase and out of phase signals are provided via lines 126 and 128, respectively, to the rest of the circuitry making up the system.

Turning now to FIGS. 5 and 6, there is shown an alternative preferred embodiment of a catheter 300 constructed in accordance with this invention. The catheter 300 is a multi-contact catheter tip according to a further aspect of the invention. In this aspect, the catheter tip 300 contains a plurality of electrodes 302.

As should be appreciated by those skilled in the art, the direction or angle of approach of the distal end of the catheter with the myocardium is not known beforehand and it may even change during the mapping procedure. Thus, the catheter 300 includes a large number (e.g., 20-200) of small electrodes 302 spaced over the rounded distal end of the catheter tip and along contiguous portions on the sides near the tip. Those electrodes are configurable so that some, e.g., a subset of them, can be set to form the sensor electrode and others the guard electrode, depending upon which are in contact with the cardiac tissue to be measured. A computer, forming a portion of the system of which the catheter is a part, is connected to those various electrodes 302 to measure the signal at each of them. In so doing it can detect which electrodes are in contact with the myocardium during any given measurement according to their measured impedance. The computer is arranged so that in conjunction with associated software or firmware, it can then automatically define the subset of the electrodes, e.g., contiguous electrodes in the central region of the contact area, collectively, as the sensor or recording electrode and a subset of those electrodes in the peripheral contact region of the contact area as being the guard electrode. Then, effectively, the guard electrode is set up automatically by the software/firmware and is connected to the follower amplifier output, again to prevent shunt resistance from reducing the amplitude and fidelity of the signal.

In one exemplary embodiment of a system constructed in accordance with this invention, an integrated circuit 304 (FIG. 6) is located in the catheter tip and connected to each of the electrodes 302. The integrated circuit 304 provides signal conditioning and multiplexing, such that only a few wires are necessary along the length of the catheter itself to convey the information provided by the many sensor electrodes to the computer (not shown).

FIG. 7 shows an exemplary circuit 400 for connecting the signal generator and follower amplifier of FIG. 3 to a plurality of electrodes 302 of a catheter like catheter 300. In the diagram of FIG. 7 only three electrodes of the large number of electrodes forming the tip are shown. Those three electrodes are designated as 302A, 302B and 302N, it being understood that there are N number of electrodes 302 and each is connected in a manner similar to that shown by the three representative electrodes 302A, 302B and 302N. This configuration allows each of the electrodes 302A, 302B, and 302N to be connected or configured as either a sensor electrode, or a guard electrode, or disconnected. Circuit operation is as described above for FIG. 3, except that each of the electrodes 302A, 302B, and 302N is connected to a respective pair of computer controlled CMOS analog switches, namely: 304A, 304B; 306A, 306B; and 308A, 308B; respectively. Closing an "A" designated switch causes the associated electrode 302 to be set up as a sensor electrode, whereas closing a "B" designated switch causes the associated electrode 302 to be connected as the guard electrode. In this manner each electrode is software/firmware configurable (i.e., becomes a "virtual" electrode) in that it/they can be individually assigned and reassigned as determined by the computer or other processor, which is monitoring the impedance of each of the electrodes. The resulting virtual sensor electrode and virtual guard electrode operate in a manner similar to that discussed above, i.e., they negate shunt current through the bulk blood, thereby increasing the accuracy of the measurements.

As should be appreciated by those skilled in the art an integrated circuit comprising the CMOS switches, the voltage follower and buffer amplifier as well as digital components for receiving serial data can be positioned at the catheter tip, thus minimizing the number of wires in the catheter. In fact, all of the electronics shown in FIG. 7 can be placed in an integrated circuit at the catheter tip, with only power and one or two data lines travelling in the catheter itself back to the system's base station computer or processor. FIG. 6 shows an exemplary multi-electrode catheter tip 300 with such an integrated circuit mounted behind the electrodes.

Another aspect of this invention entails a catheter system for identifying regions of maximal cardiac tissue stretch to help identify and localize regions of focal firing, to direct radio frequency to lesions for ablation. As is known, focal atrial tachycardia (AT) have specific well recognized sites of origin in both atria which include the mitral and tricuspid annuli, the pulmonary vein orifices, the insertions of the superior and inferior vena cavae, and the ostium of the coronary sinus. All of these sites are at the junctions of atrial muscle tissue with tissue of significantly increased mechanical stiffness, e.g., the fibrous tissue of the AV valve rings or the collagen support layer of the great veins. These stiffer structures confer increased loading conditions on the atrial muscle tissue, particularly on the adjacent strips of atrial muscle, causing increased stretch of these muscle layers. The increased stretch has two electro-physiologic effects. First, the increased stretch causes greater opening probability and current flow through so-called stretch activated or mechano-gated ion channels, many of which carry depolarizing currents (e.g., L-type $Ca^{+2}$ channels, mechano-gated sodium channels, and Na/Ca exchanger pumps) that can generate after-depolarizations. Second, the increased loading in these adjacent muscle strips results in to shortened action potential durations and consequent shortened refractoriness. This allows sarcoplasmic $Ca^{+2}$ concentrations, which can drive $Ca^{+2}$-activated depolarizing currents, to persist beyond repolarization and therefore generate unopposed depolarizing inward currents with resultant focal firing.

Thus, in accordance with another embodiment of the catheter systems of this invention, the tip of the catheter can include a pressure sensing device. Such a pressure sensing catheter enables the system to map tissue stiffness throughout the atrium. In particular, in this embodiment the system includes a mechanical stiffness detector to map the tissue mechanical compliance at high spatial resolution, with compliance being the reciprocal of stiffness (i.e., compliance=1/stiffness). This measurement may be displayed on an electro-anatomic mechanical compliance map which could, in turn, help to localize regions of focal firing and direct deployment of radio frequency lesions for ablation.

Still another aspect of this invention entails a catheter system including a controller for time-gated recording of impedance. In particular, such a system is adapted to be configured for gating the impedance measurement to electrical systole and diastole, and sub-intervals within systole and diastole, to separate out the membrane current flows during rest and activation to more accurately identify anisotropically conducting tissue from normally conducting tissue to thereby help identify functional boundaries of critical isthmuses of atypical reentrant circuits. In particular, the software/firmware of the system can be arranged so that measurements of impedance, both in phase and out of phase, are synchronized to the cardiac cycle by timing brief periods of recording at intervals after the beat starts, e.g., triggered on the P wave of the electrocardiogram for atrial arrhythmias or the QRS complex for ventricular arrhythmias. Repeated 5-10 intervals of this type can separately determine the impedance in early and late diastole, during the action potential upstroke, during early and late plateau, and during final repolarization. Each of these intervals should provide information characteristic of different events and different states of particular membrane channels. By averaging intervals over repeat cycles of the cardiac rhythm, the fluctuations or uncertainty of each short interval can be reduced to values leading to reliable determination of impedance during that part of the cycle.

Yet another aspect of this invention entails a time-gated electrode configuration. In particular, a catheter comprising the multiple configurable electrodes, like the catheter 300 of FIGS. 5 and 6, can have a subset of its electrodes 302 configured into a virtual sensing electrode and another subset of its electrodes configured into a virtual guard electrode, with such configuration and reconfiguration being accomplished dynamically during the cardiac cycle by the software/firmware of the system. In particular, once measurements are made of which electrodes are contacting the myocardium as a function of time during the cardiac cycle, then the configuration map can be applied dynamically as triggered from an electrocardiogram or other cardiac cycle-specific control signals.

Thus, as should be appreciated by those skilled in the art, by utilizing the above described synchronized gating techniques, the optimization of the recording and the recording itself can be temporally improved.

Without further elaboration, the foregoing will so fully illustrate our invention that others may, by applying current or future knowledge adopt the same for use under various conditions of service.

We claim:

1. A catheter system for detecting at least one electrical property of anisotropically conducting cardiac tissue of a living being in an area of the tissue comprising surrounding blood having electrical conductance, said system comprising
   a catheter having a distal end comprising
      a plurality of electrodes configured for engaging the cardiac tissue for effecting high density impedance mapping thereof,
      and an electrical shield,
   said distal end of said catheter being arranged to reduce shunt conductance which exists between the electrodes and the surrounding blood,
   said system further comprising control circuitry configured to measure electrical impedance between pairs of said plurality of electrodes or between each of said plurality of electrodes and ground and to determine based on said impedance which of said electrodes are in contact with the cardiac tissue,
   said control circuitry further configured to connect a first subset of said plurality of electrodes to a sensing circuit, said sensing circuit configured to measure a voltage at at least one electrode of said first subset of said plurality of electrodes,
   said control circuitry further configured to connect a second subset of said plurality of electrodes as guard electrodes that are connected to a follower amplifier configured to apply a signal to said guard electrodes to maintain the potential of said guard electrodes at the same voltage as the voltage appearing at said at least one sensing electrode,
   said guard electrodes surrounding said first subset of electrodes and configured to engage said cardiac tissue and shield said first subset of electrodes from the surrounding blood adjacent the cardiac tissue, said electrical shield surrounding said guard electrodes.

2. The catheter system of claim 1 additionally comprising a signal source, said signal source applying a small current to said first subset of electrodes, whereupon a sensed voltage occurs at said first subset of electrodes that is indicative of impedance of the cardiac tissue in the vicinity of said first subset of electrodes.

3. The system of claim 1 wherein the catheter is limited in size so as to be arranged to measure the impedance at a plurality of points on the cardiac tissue at a density of at least four points/cm$^2$.

4. The system of claim 1, wherein said impedance is measured with a time-varying signal so as to measure in phase and quadrature components of said impedance.

5. The system of claim 1, wherein said control circuitry is configured to dynamically reconfigure said first and second subsets of electrodes during a cardiac cycle wherein motions of the tissue or catheter alter which portions of the plurality of electrodes are in firm contact with the tissue.

* * * * *